United States Patent [19]

Guseinov et al.

[11] 4,244,892

[45] Jan. 13, 1981

[54] PROCESS FOR PREPARING ALLYL CHLORIDE

[76] Inventors: Nazim M. O. Guseinov, ulitsa Gusi-Gudzhieva, 3, kv. 12; Vagab S. Aliev, ulitsa Nizami, 66, blok 5, kv. 40; Alish I. Mustafaev, ulitsa Gagarina, 23, kv. 3, all of Baku; Vladimir M. Zimin, 10 proezd Mariinoi Roschi, 13, kv. 251, Moscow; Rafael S. Sverdlov, Rabochy prospekt, 5, kv. 6; Nina G. Shkondina, prospekt 50 let VLKSM, 5, kv. 39, both of Baku; Eleonora E. Chianurashvili, ulitsa Schepkina, 4, Moscow; Margarita K. Morozova, ulitsa Nizami, 66, kv. 69; Rasim S. O. Mirzoev, ulitsa Musevi 4 kv. 12, both of Baku; Gabil S. O. Sharifov, 5 Mikroraion, 2, kv. 6, Sumgait; Ramiz A. Dzhabiev, 4 Mikroraion, ulitsa Koltsevaya, 62, kv. 80, Baku; Leonid A. Oshin, ulitsa Shkuleva, 3, kv. 107; Lemel S. Genin, ulitsa Junykh Lenintsev, 82, kv. 19, both of Moscow, all of U.S.S.R.

[21] Appl. No.: 12,453

[22] Filed: Feb. 15, 1979

[30] Foreign Application Priority Data

Feb. 16, 1978 [SU] U.S.S.R. .............................. 2585604

[51] Int. Cl.$^3$ .............................................. C07C 21/00
[52] U.S. Cl. ................................................... 570/223
[58] Field of Search ................................... 260/654 R

[56] References Cited

U.S. PATENT DOCUMENTS

3,865,886   2/1975   Schindler et al. ............... 260/654 R

FOREIGN PATENT DOCUMENTS

| 413816 | 12/1966 | France ................. 260/654 R |
| 48-40323 | 11/1973 | Japan .................. 260/654 R |
| 363680 | 12/1972 | U.S.S.R. ............... 260/654 R |
| 525655 | 10/1976 | U.S.S.R. ............... 260/654 R |

*Primary Examiner*—Helen M. S. Sneed
*Attorney, Agent, or Firm*—Lackenbach, Lilling & Siegel

[57] ABSTRACT

In accordance with the present invention, the process for preparing allyl chloride comprises chlorination of propylene with hydrogen chloride in an upward stream consisting of propylene, hydrogen chloride and a catalyst, i.e. manganese dioxide incorporated in a leaned manganese ore in an amount of 20 to 35% byu weight at a temperature within the range of from 300° to 500° C., concentration of the catalyst in the stream of 130–180 kg/m$^3$, time of contact between propylene, hydrogen chloride and the catalyst in the stream of 0.2–0.7 sec and a volume ratio between propylene and hydrogen chloride in the stream of 1:3–5 respectively. Then the spent catalyst is separated from the reaction mixture resulting from chlorination, regenerated with oxygen at a temperature of from 500° to 520° C. and recycled to the chlorination process. The process according to the present invention makes it possible to achieve a yield of allyl chloride of up to 81.5 vol. % as calculated for the passed propylene, conversion of propylene of up to 98.0% at a process selectivity of from 80 to 85 vol. %. Furthermore, the process according to the present invention makes it possible to provide a wasteless production of allyl chloride.

4 Claims, 1 Drawing Figure

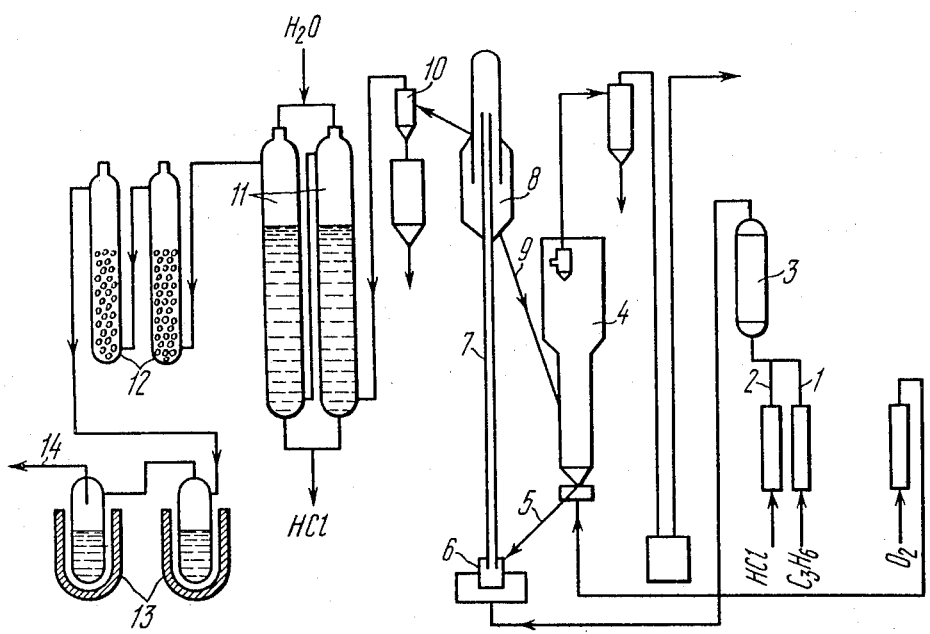

PROCESS FOR PREPARING ALLYL CHLORIDE

FIELD OF THE INVENTION

The present invention relates to processes for the preparation of chlorinated organic products and, more specifically, to processes for preparing allyl chloride which is useful in the production of synthetic glycerol, allyl alcohol, epichlorohydrin, dichlorohydrin and employed in the manufacture of synthetic resins.

BACKGROUND OF THE INVENTION

Known in the art are various processes for the preparation of allyl chloride.

Thus, known is a process for preparing allyl chloride by thermal gas-phase chlorination of propylene by means of gaseous chlorine at a temperature ranging from 500° to 510° C. The process is carried out in a hollow or partitioned cylindrical apparatus by mixing propylene heated to a temperature of from 340° to 360° C. with cold evaporated high-concentration chlorine with a 6-fold excess of propylene. The reaction product effluent from the reactor is subjected to an abrupt cooling-quenching to inhibit undesirable secondary processes, and is then separated in condensation-stripping columns sprayed by liquid propylene (cf. L. Oshin "Manufacture of Synthetic Glycerol", Moscow, "Khimija" Publishing House, 1974).

Main disadvantages of the above-described prior art process reside in a low yield of allyl chloride and a low conversion of the starting feed equal to 17.8%, a high recycle ratio of propylene (thus, out of 6 volumes of propylene supplied for the reaction 5 volumes are recycled) thus resulting in increased power consumption and losses of propylene. Furthermore, disadvantages of the process are limited product output from a unit working space of the reactor, low capacity of the apparatus, non-efficient utilization of rather expensive chlorine half of which is consumed for the formation of hydrogen chloride.

Also known in the art is a process for preparing allyl chloride by way of oxidizing chlorination of propylene with hydrogen chloride in the presence of air oxygen (cf. U.S. Pat. No. 2,966,515). The starting mixture is passed at a temperature ranging from 300° to 500° C. through a stationary catalyst bed i.e. lithium chloride supported on pumice; the contact time being equal to 0.5-12 sec. The components are taken in the ratio of 1:1:2.5 (propylene:hydrogen chloride:oxygen or air respectively). 90 mol. % of allyl chloride is present in the condensed reaction products.

Also known in the art is a process for preparing allyl chloride by oxidizing chlorination of propylene by means of hydrogen chloride and air oxygen in the presence of catalysts consisting of a mixture of chlorides of different metals (zinc, palladium, copper, potassium, lithium, magnesium, barium, iron, calcium).

The process of oxidizing chlorination is conducted mainly in tubular reactors with a stationary or fluidized bed of catalyst at a temperature within a wide range of from 50° to 500° C. The catalyst is used in the form of granules manufactured from mixtures of different chlorides and in the form of carrier-supported chlorides (pumice, silica gel and the like materials are used as the carrier; cf. USSR Inventor's Certificate No. 363680 published in 1972).

The process according to said USSR Inventor's Certificate is carried out in a reactor with a fluidized bed of a finely divided catalyst consisting, for example, of a mixture of chlorides of palladium, copper, zinc and potassium taken in the molar ratio of 0.1:1:1:1 respectively, deposited onto a carrier, i.e. silica gel. The weight content of palladium in the catalyst should be obligatorily within the limits of 0.3-0.4%.

The yield of allyl chloride as calculated for the passed propylene is 4 to 6%.

Principal disadvantages of the above-discussed prior art processes are: rapid activity drop of the catalyst due to high volatility of metal chlorides and related low yields of allyl chloride causing additional technological troubles at the stage of recovery of allyl chloride from the contact gas, as well as difficulties associated with temperature control in the fluidized bed.

The closest prior art process most resembling that of the present invention (prototype) is the process for preparing allyl chloride by way of oxidizing chlorination of propylene with hydrogen chloride in the presence of air and a manganese dioxide catalyst incorporated in a leaned manganese ore in an amount of from 26 to 28% by weight (cf. USSR Inventor's Certificate No. 525,655). The oxidizing chlorination process is conducted in a stationary bed of catalyst with the ratio of $HCl:C_3H_6:air = 1:1:8$ respectively and at a temperature in the reaction zone varied within the range of from 350° to 450° C.

The yield of alkyl chloride in this process, as calculated for the passed propylene is 28.9 vol.% with a selectivity of 85.3% and conversion of propylene of 34%.

Principal disadvantages of this prior art process are: low yield of allyl chloride and low conversion of propylene; a high degree of dilution of the starting raw materials and the reaction products with air (80% by volume), which hinders isolation of the desired product and restricts the process productivity.

Furthermore, disadvantages of the process also are in inevitable combustion of a portion of propylene to $CO_2$ in connection with the presence of air oxygen in the reaction zone and difficulties associated with organization of an efficient heat removal and control of temperature inside the stationary bed of the catalyst.

SUMMARY OF THE INVENTION

It is an object of the present invention to provide a process for preparing allyl chloride which makes it possible to increase the yield of allyl chloride and conversion of the starting materials.

This object is accomplished by a process for preparing allyl chloride by chlorination of propylene with hydrogen chloride at a temperature ranging from 300° to 500° C. in the presence of a catalyst, i.e. manganese dioxide incorporated in a leaned manganese ore in an amount of from 20 to 35% by weight. In accordance with the present invention said chlorination is effected in an ascending stream consisting of propylene, hydrogen chloride and the above-mentioned catalyst; the catalyst concentration in the stream is equal to 130-180kg/m³. The time of contact between propylene, hydrogen chloride and the catalyst in said stream is within the range of from 0.2 to 0.7 sec and the volume ratio between propylene and hydrogen chloride in the stream is 1:3-5 respectively. Thereafter, the spent catalyst is separated from the reaction mixture resulting from chlorination, the catalyst is regenerated by oxygen at a temperature of from 500° to 520° C. and recycled to the process of chlorination of propylene.

DETAILED DESCRIPTION OF THE INVENTION

The process according to the present invention is effected in the following manner, reference being made to the accompanying drawing.

Propylene via a pipeline 1 and hydrogen chloride via a pipeline 2 are supplied into a mixing vessel 3 in such an amount that in the resulting mixture a volume ratio between propylene and hydrogen chloride is equal to 1:3-5 respectively. A greater amount of hydrogen chloride is inadvisable to feed into the reaction mixture, since the above-specified amount of hydrogen chloride is sufficient to achieve maximum conversion.

A catalyst preheated to a temperature of from 500° to 520° C. in a reactor 4 of regeneration and comprising manganese dioxide incorporated in a leaned manganese ore in an amount of from 20 to 35% by weight (the ore particle size is 0.5-1 mm) is continuously supplied via a line 5 into a mixing chamber 6. To the same mixing chamber 6 the mixture of propylene and hydrogen chloride is fed from the mixing vessel 3. From the mixing chamber 6 the mixture consisting of propylene, hydrogen chloride and the catalyst is supplied in an ascending flow to a chlorination reactor 7. The catalyst concentration in the stream is 130 to 180 kg/m$^3$. Chlorination is conducted at a temperature within the range of from 400° to 500° C. and a time of contact between propylene, hydrogen chloride and the catalyst of from 0.2 to 0.7 sec.

In the chlorination reactor 7 in the ascending stream of the gas-catalyst mixture chlorination of propylene occurs according to the following scheme:

$$MnO_2 + 4HCl \rightarrow MnCl_2 + Cl_2 + 2H_2O \quad (I)$$

$$C_3H_7 + Cl_2 \rightarrow C_3H_6Cl + HCl \quad (II)$$

The reaction products at the outlet of the chlorination reactor 7 are passed to a separator 8, wherein the reaction products are separated from the spent catalyst. The latter is discharged, via a chute 9, to the regeneration reactor 4. In the regeneration reactor 4 the spent catalyst as $MnCl_2$ with the valence $Mn^{+2}$ is oxidized by oxygen to its initial active form $MnO_2$ with the valence $Mn^{+4}$ with evolution of chlorine (gaseous) according to the following reaction scheme:

$$MnCl_2 + O_2 \rightarrow MnO_2 + Cl_2 \quad (III)$$

The regenerated catalyst is then delivered to the mixing chamber 6 via the line 5. In this manner a continuous circulation of the catalyst is effected in a closed system.

One embodiment of separation of the reaction mixture is as follows:

The reaction mixture containing allyl chloride, the unreacted propylene and hydrogen chloride, water and propylene chloroderivatives is passed through a dust-separator 10 and further in two water-sprayed columns 11 for absorption of the unreacted hydrogen chloride and water. Then the mixture of allyl chloride, propylene chloroderivatives and the unreacted propylene is subjected to drying in columns 12 filled with calcium chloride. In traps 13 chloroderivatives of propylene and allyl chloride are condensed. From the traps 13 the noncondensed unreacted propylene can be recycled via line 14. A mixture of allyl chloride and chloroderivatives of propylene is separated by rectification.

Chlorine formed in the regeneration reactor 4 is used to its purpose.

In the process according to the present invention the yield of allyl chloride as calculated for the passed propylene is as high as 71.0-81.5 vol.%; conversion of propylene and hydrogen chloride is equal to 90-98% and the process selectivity is 80-85 vol. %.

Therefore, the process according to the present invention has the following advantages over the prior art process according to USSR Inventor's Certificate No. 525,655; the yield of allyl chloride is increased by 49.5 vol. % and propylene conversion is increased by 62.5%.

Due to the fact that the chlorination process is conducted in a moving stream of catalyst with a continuous circulation thereof between two reactors: chlorination reactor 7 and regeneration reactor 4, the oxidizing-reducing properties of the catalyst are used to the fullest possible extent.

In the zone of regeneration of the spent catalyst, conditions are provided for the production of gaseous chlorine which can be used as a chlorination agent in processes of organic synthesis (production of sulphanol, epichlorohydrin, dichloroethane and the like).

In the chlorination zone there is no necessity of supplying an oxidation agent-air. This results in increased process productivity, production of a concentrated reaction mass which can be supplied, without separation, to the synthesis of a concentrated dichlorohydrin.

For a better understanding of the present invention the following specific Examples are given hereinbelow by way of illustration.

EXAMPLE 1

A reaction mixture from the mixing vessel 3 in the amount of 750 l/h containing propylene and hydrogen chloride in a volume ratio of 1:3 is fed to the mixing chamber 6.

A leaned manganese ore preheated in the regeneration reactor to a temperature of 500° C. and having a particle size of from 0.5 to 1 mm and the following composition, percent by weight: $MnO_2$ 20.0; $Fe_2O_3$ 3.00; $Al_2O_3$ 16; CaO 9; $SiO_2$ 50; water being the balance, is supplied via the line 5 to the mixing chamber 6. The mixture consisting of propylene, hydrogen chloride and a catalyst is fed in an upward stream to the chlorination reactor 7. The contact time of the reaction mixture with the catalyst in the chlorination reactor 7 is equal to 0.6 sec, while the catalyst concentration is 180 kg/m$^3$. The chlorination process is conducted at a temperature of 400° C. The reaction products at the outlet of the chlorination reactor 7 are fed to the separator 8, wherein the reaction products are separated from the spent catalyst. The latter is discharged to the regeneration reactor 4 via the chute 9. In the regeneration reactor 4 the spent catalyst in the form of $MnCl_2$ with a valence of $Mn^{+2}$ is oxidized with oxygen to its initial active form $MnO_2$ with a valence $Mn^{+4}$ and evolution of gaseous chlorine occurs according to the reaction:

$$MnCl_2 + O_2 \rightarrow MnO_2 + Cl_2 \quad (III)$$

The regenerated catalyst is then fed, via the line 5, to the mixing chamber 6.

As a result of chlorination a reaction mixture is obtained having the following composition, percent by volume:

| | |
|---|---|
| allyl chloride | 13.02 |
| monochloroderivatives of propylene | 3.98 |
| dichloroderivatives of propylene | 0.71 |
| unreacted propylene | 7.29 |
| unreacted hydrogen chloride | 11.25 |
| water | 26.0 |
| HCl for the formation of $MnCl_2$ | 37.75. |

The reaction mixture of the above-mentioned composition is passed through the dust-separator 10 and then into two water-sprayed columns 11 for absorption of the unreacted hydrogen chloride and water. Then a mixture of allyl chloride, propylene chloroderivatives and the unreacted propylene is dried in columns 12 packed with calcium chloride. In traps 13 allyl chloride and propylene chloroderivatives are condensed.

From the traps 13 the non-condensed unreacted propylene can be recycled via the line 14. The mixture of allyl chloride and propylene chloroderivatives is separated by rectification.

Chlorine formed in the regeneration reactor 4 is delivered to the use thereof.

On completion of the process the following data are obtained:

| | |
|---|---|
| Propylene conversion | 70.8 vol. % |
| Conversion of hydrogen chloride with account of chlorination of propylene and the catalyst | 3.0 vol. % |
| Yield of allyl chloride as calculated for the passed propylene | 52.1 vol. % |
| Amount of the resulting gaseous chlorine as calculated for the passed hydrogen chloride | 7.5 vol. %. |

EXAMPLE 2

The process is carried out in a manner similar to that described in the foregoing Example 1, except that the ratio between the starting component $C_3H_6$ and HCl in this Example is equal to 1:4, concentration of the catalyst is 130 kg/m$^3$ and the temperature in the reactor for the catalyst regeneration is 520° C.

| | percent by volume |
|---|---|
| Supplied to the reaction: | |
| Propylene | 20.0 |
| Hydrogen chloride | 80.0 |
| Obtained in the reaction: | |
| Allyl chloride | 14.5 |
| Propylene monochloroderivatives | 3.62 |
| Propylene dichloroderivatives | 0.06 |
| Unreacted propylene | 1.82 |
| Unreacted HCl | 8.0 |
| Water | 29.0 |
| HCl for the formation of $MnCl_2$ | 43.0. |

On completion of the process the following data are obtained:

| | percent by volume |
|---|---|
| Propylene conversion | 90.0 |
| Conversion of hydrogen chloride with account of chlorination of propylene and the catalyst | 90.0 |
| Selectivity of the process | 79.5 |
| Yield of allyl chloride per the passed propylene | 72.5 |
| Amount of gaseous chlorine formed in the process as calculated for the passed HCl | 10.1. |

EXAMPLE 3

The process is carried out by following the procedure of Example 1 hereinbefore, except that in this Example the chlorination temperature is equal to 420° C. and the ratio between the starting components $C_3H_6$ and HCl is equal to 1:4.

| | percent by volume |
|---|---|
| Supplied to the reaction | |
| Propylene | 20.0 |
| Hydrogen chloride | 80.0 |
| Obtained in the reaction | |
| Allyl chloride | 15.7 |
| Propylene monochloroderivatives | 3.25 |
| Propylene dichloroderivatives | 0.55 |
| Unreacted propylene | 0.50 |
| Unreacted hydrogen chloride | 1.60 |
| Water | 31.4 |
| HCl for the formation of $MnCl_2$ | 47.0. |

On completion of the process the following data are obtained:

| | percent by volume |
|---|---|
| Conversion of propylene | 97.5 |
| Conversion of hydrogen chloride with account of chlorination of propylene and the catalyst | 98.0 |
| Process selectivity | 80.5 |
| Yield of allyl chloride per the passed propylene | 78.5 |
| Amount of gaseous chlorine formed in the process as calculated for the passed hydrogen chloride | 11.8. |

EXAMPLE 4

The process is carried out as in Example 1 hereinbefore, except that the chlorination temperature in this Example is equal to 450° C.

| | percent by volume |
|---|---|
| Supplied to the reaction | |
| Propylene | 20.0 |
| Hydrogen chloride | 80.0 |
| Obtained in the reaction | |
| Allyl chloride | 14.22 |
| Propylene monochloroderivatives | 2.24 |
| Propylene dichloroderivatives | 0.54 |
| Unreacted propylene | 1.0 |
| Unreacted hydrogen chloride | 6.4 |
| Water | 18.44 |
| HCl for the formation of $MnCl_2$ | 47.16. |

On completion of the process the following data are obtained:

| | percent by volume |
|---|---|
| Conversion of propylene | 95.0 |
| Conversion of hydrogen chloride with the account of consumption thereof for chlorination of propylene and the catalyst | 92.0 |

-continued

| | percent by volume |
|---|---|
| Selectivity of the process | 83.5 |
| Yield of allyl chloride as calculated for the passed propylene | 71.1 |
| Amount of gaseous chlorine formed in the process as calculated for the passed hydrogen chloride | 11.3. |

EXAMPLE 5

The procedure of the foregoing Example 1 is repeated, except the ratio between the starring components which in this Example is equal to $C_3H_6:HCl = 1:5$ and the temperature of the chlorination reaction is 450° C.

| | percent by volume |
|---|---|
| Supplied to the reaction | |
| Propylene | 16.7 |
| Hydrogen chloride | 83.3 |
| Obtained in the reaction | |
| Allyl chloride | 13.61 |
| Propylene monochloroderivatives | 2.36 |
| Propylene dichloroderivatives | 0.07 |
| Unreacted propylene | 0.76 |
| Unreacted hydrogen chloride | 4.20 |
| Water | 27.22 |
| HCl for the formation of $MnCl_2$ | 51.78. |

On completion of the process the following data are obtained:

| | percent by volume |
|---|---|
| Conversion of propylene | 95.4 |
| Conversion of hydrogen chloride with the account of consumption thereof for chlorination of propylene and the catalyst | 95.0 |
| Selectivity of the process | 85.0 |
| Yield of allyl chloride as calculated for the passed propylene | 81.5 |
| Amount of chlorine resulting in the process as calculated for the passed hydrogen chloride | 13.3. |

EXAMPLE 6

The process is conducted in a manner similar to that described in Example 1, except that the reaction mixture is delivered from the mixing vessel 3 (the mixture contains propylene and hydrogen chloride in the ratio of 1:4) in the amount of 1,000 l/h into the mixing chamber 6; the time of contact between said mixture and the catalyst in the chlorination reactor 7 to equal to 0.3 sec, and the chlorination temperature is 450° C.

| | percent by volume |
|---|---|
| Supplied to the reaction | |
| Propylene | 20 |
| Hydrogen chloride | 80 |
| Obtained in the reaction | |
| Allyl chloride | 13.0 |
| Propylene monochloroderivatives | 2.36 |
| Propylene dichloroderivatives | 0.95 |
| Unreacted propylene | 4.16 |
| Unreacted hydrogen chloride | 8.24 |
| water | 26.0 |
| HCl for the formation of $MnCl_2$ | 45.29 |

On completion of the process the following data are obtained:

| | percent by volume |
|---|---|
| Conversion of propylene | 79.2 |
| Conversion of hydrogen chloride with the account of consumption thereof for chlorination of propylene and the catalyst | 89.7 |
| Selectivity of the process | 79.7 |
| Yield of allyl chloride as calculated for the passed propylene | 65.0 |
| Amount of gaseous chlorine formed in the process as calculated for the passed hydrogen chloride | 9.8. |

EXAMPLE 7

The process is conducted following the procedure of Example 1 hereinbefore, except that the chlorination temperature in this Example is equal to 450° C. and the composition of the leaned manganese ore which is the following, percent by weight: $MnO_2$ 28, $Fe_2O_3$ 3, $Al_2O_3$ 16, CaO 9, $SiO_2$ 42, water being the balance.

| | percent by volume |
|---|---|
| Supplied to the reaction | |
| Propylene | 20 |
| Hydrogen chloride | 80 |
| Obtained in the reaction | |
| Allyl chloride | 15.7 |
| Propylene monochloroderivatives | 3.25 |
| Propylene dichloroderivatives | 0.55 |
| Unreacted propylene | 0.50 |
| Unreacted hydrogen chloride | 1.60 |
| Water | 31.4 |
| HCl for the formation of $MnCl_2$ | 45.29 |

On completion of the process the following data are obtained:

| | percent by volume |
|---|---|
| Conversion of propylene | 79.2 |
| Conversion of hydrogen chloride with the account of consumption thereof for chlorination of propylene and the catalyst | 89.7 |
| Process selectivity | 79.7 |
| Yield of allyl chloride as calculated for the passed propylene | 65.0 |
| Amount of gaseous chlorine formed in the process as calculated for the passed hydrogen chloride | 9.8. |

EXAMPLE 7

The process is carried out as in Example 1, except the chlorination temperature which in this Example is equal to 450° C. and the composition of a leaned manganese ore which is the following; percent by weight: $MnO_2$ 28; $Fe_2O_3$ 3; $Al_2O_3$ 16; CaO 9; $SiO_2$ 42, water being the balance.

| | percent by volume |
|---|---|
| Supplied to the reaction | |
| Propylene | 20 |
| Hydrogen chloride | 80 |
| Obtained in the reaction | |
| Allyl chloride | 15.7 |
| Propylene monochloroderivatives | 3.25 |
| Propylene dichloroderivatives | 0.55 |
| Unreacted propylene | 0.50 |
| Unreacted hydrogen chloride | 1.60 |
| Water | 31.4 |
| HCl for the formation of $MnCl_2$ | 47.0. |

On completion of the process the following data are obtained:

| | |
|---|---|
| Conversion of propylene | 97.5 vol.% |
| Conversion of hydrogen chloride with the account of consumption thereof for chlorination of propylene and the catalyst | 98.0 vol.%. |
| Selectivity of the process | 80.5 vol.% |
| Yield of allyl chloride as calculated for the passed propylene | |
| Amount of gaseous chlorine formed in the process as calculated for the passed hydrogen chloride | 11.8 vol.%. |

Example 8

The process is carried out in a manner similar to that of Example 1 hereinbefore, except the chlorination reaction temperature which in this Example is equal to 450° C. and the composition of a leaned manganese ore which is the following percent by weight: $MnO_2$—35; $Fe_2O_3$—3; $Al_2O_3$—16; CaO—9; $SiO_2$—35; water being the balance.

| Supplied to the reaction | percent by volume |
|---|---|
| Propylene | 16.7 |
| Hydrogen chloride | 83.3 |
| Obtained in the reaction | percent by weight |
| Allyl chloride | 13.61 |
| Propylene monochloroderivatives | 2.36 |
| Propylene dichloroderivatives | 0.07 |
| Unreacted propylene | 0.76 |
| Unreacted hydrogen chloride | 4.20 |
| Water | 27.22 |
| HCl for the formation of $MnCl_2$ | 51.78. |
| On completion of the process the following data are obtained | |
| Conversion of propylene | 95.4 vol.% |
| Conversion of hydrogen chloride with the account of consumption thereof for chlorination of propylene and the catalyst | 95.0 vol.% |
| Selectivity of the process | 85.0 vol.% |
| Yield of allyl chloride as calculated for the passed propylene | 81.5 vol.% |
| Amount of the resulting gaseous chlorine formed in the process as calculated for the passed hydrogen chloride | 13.3 vol.%. |

What is claimed is:

1. A process for preparing allyl chloride comprising chlorination of propylene by hydrogen chloride in an upward stream consisting of propylene, hydrogen chloride and a catalyst which is manganese dioxide incorporated in leaned manganese ore in an amount of from 20 to 35% by weight at a temperature ranging from 300° to 500° C., the catalyst concentration in said stream being 130 to 180 kg/m³, the time of contact between propylene, hydrogen chloride and the catalyst in the stream being 0.2 to 0.7 sec, volume ratio between propylene and hydrogen chloride in the stream being 1:3-5 respectively, followed by separation of the spent catalyst from the reaction mixture resulting from chlorination, regeneration of said catalyst by oxygen at a temperature ranging from 500° to 520° C. and recycling thereof to the process of propylene chlorination.

2. The process of claim 1, wherein the particle size of the leaned manganese ore varies from about 0.5 to 1 mm.

3. The process of claim 1, wherein the chlorination of propylene occurs in accordance with the following reactions:

$$MnO_2 + 4HCl \rightarrow MnCl_2 + Cl_2 + 2H_2O \qquad (I)$$

$$C_3H_6 + Cl_2 \rightarrow C_3H_5Cl + HCl \qquad (II)$$

4. The process of claim 1, wherein the yield of allyl chloride as calculated for the passed propylene is about 71.0–81.5 vol. %, the conversion of propylene and hydrogen chloride is about 90–98% and the process selectivity is about 80–85 vol. %.

* * * * *